United States Patent [19]

Warchol et al.

[11] Patent Number: 5,162,110
[45] Date of Patent: Nov. 10, 1992

[54] BINDING THEOPHYLLINE TO ION EXCHANGE RESINS

[75] Inventors: Mark P. Warchol, Ambler; Zofia J. Chrzan, Sellersville, both of Pa.

[73] Assignee: Rhône-Poulenc Rorer Pharmaceuticals Inc., Collegeville, Pa.

[21] Appl. No.: 629,833

[22] Filed: Dec. 19, 1990

[51] Int. Cl.$^5$ .................. A61K 31/74; A61K 9/14
[52] U.S. Cl. ........................... 424/78.15; 424/78.1
[58] Field of Search ...................... 424/79, 78.15

[56] References Cited

U.S. PATENT DOCUMENTS

| | | | |
|---|---|---|---|
| 3,109,775 | 11/1963 | Shepard et al. | 514/265 |
| 3,143,465 | 8/1964 | Keating | 424/79 |
| 3,594,470 | 7/1971 | Borodkin et al. | 424/79 |
| 4,261,970 | 4/1981 | Ogawa et al. | 514/263 |
| 4,996,047 | 2/1991 | Kelleher et al. | 424/483 |

FOREIGN PATENT DOCUMENTS 2246037  4/1974  Fed. Rep. of Germany ........ 424/79

Primary Examiner—Thurman K. Page
Assistant Examiner—Peter F. Kulkosky
Attorney, Agent, or Firm—Martin F. Savitzky; James A. Nicholson; Alexis Barron

[57] ABSTRACT

In a method in which an ionizable pharmaceutical material, such as theophylline, having a pharmaceutically-active anionic group is bonded to an anion exchange resin having cationic groups bonded to displacable anionic groups by bringing said material and said resin into contact with each other under conditions such that the pharmaceutically-active anionic group of said material is bonded to the cationic group of said resin and replaces the anionic group thereof, the improvement comprising effecting said contact in an environment which is substantially free of carbon dioxide and/or bicarbonate ion, a pharmacologically active composition comprising said pharmaceutically active anion and said resin, including a composition in which at least about 40% of the binding capacity of the resin comprises said pharmaceutically active anion, and a sustained release pharmaceutical composition, including enteric coated particles of the composition, and stabilizing said composition by maintaining it in an environment substantially free of bicarbonate and/or carbon dioxide.

15 Claims, 2 Drawing Sheets

BINDING THEOPHYLLINE TO ION EXCHANGE RESINS

FIELD OF THE INVENTION

This invention relates to pharmaceutical compositions which are effective in releasing into the body useful drugs over a prolonged period of time. More particularly, this invention relates to the use of an ion exchange resin in the preparation of such compositions.

The present invention will be described initially in connection with its applicability to theophylline, a bronchodilator which is used to treat individuals with asthma. However, as discussed hereinbelow, it has applicability to other types of pharmaceuticals.

For many therapeutics which are administered orally, it is preferred that drug molecules be released into the body at a constant, or otherwise controlled rate, over a relatively long period of time, such as, for example, 4 to 8 hours, or longer. This can result in an overall increased effectiveness of the drug. Certain pharmaceuticals which dissolve rapidly in the stomach build up in excessive concentrations in the blood. This can cause adverse physiological effects.

The bronchodilator, theophylline, for example, is commonly administered orally. If theophylline is not administered in a sustained release form, gastrointestinal and cardiovascular side effects occur as excessive quantities are released into the stomach. It is therefore desirable to prepare such therapeutics in a form such that they survive passage through the stomach and undergo controlled release in the intestine. An "enteric-coated" pharmaceutical is a pharmaceutically-active compound which is coated with a material which delays release of the pharmaceutically-active compound until it reaches the intestines.

This invention relates to an improved technique which can be used in a process for preparing sustained-release pharmaceutical compositions, including those which contain theophylline, and to a composition made therefrom.

Reported Developments

Numerous types of sustained-release pharmaceutical compositions are known, including enteric-coated pharmaceuticals, as disclosed, for example, in U.S. Pat. Nos: 3,109,775; 4,083,949; and 4,261,970; and in PCT application bearing Publication no. WO 83/00284. Speaking generally, the aforementioned publications disclose a pharmacologically-active material encased in a slowly dissolvable coating or in a porous material which is insoluble in the acid environment of the stomach and which allows the active material to pass therethrough and into the intestine. For example, a typical sustained-release preparation comprises an inert core, such as a sugar grain, coated with an adhesive which has applied thereto a pharmacologically-active substance. The amount of active substance may be built up by forming layer upon layer of the adhesive coating and active substance. Once the desired amount of active substance has been applied, the multi-layered structure is covered with a permeable membrane which resists dissolution and otherwise being degraded in the stomach and in the intestine and which allows the desired pharmaceutical substance, for example, theophylline to pass through the permeable membrane as the pharmaceutical substance is dissolved by mildly alkaline intestinal fluids.

A sustained-release composition is disclosed in PCT application bearing Publication no. WO 87/06098, assigned to the same assignee as the present invention. In this method, seed particles are coated with a pharmaceutically-active compound such as theophylline by forming a fluidized ring of the seed particles and contacting them as they are maintained in a suspended state with a liquid composition containing the pharmaceutically-active compound and an alkali soluble material which functions as a binder. In preferred form, the coated seed particles are themselves provided with an additional coating formed from a mixture of water soluble material and an acid insoluble and alkali insoluble material not otherwise degradable in the environments of both the stomach and intestine. The water soluble material is capable of dissolving in the aqueous environment of the stomach and intestine. Such dissolution forms in the coating pores of a sufficient size to permit a pharmaceutically-active compound such as theophylline to pass through. To achieve prolonged sustained-release, the aforementioned coating is in turn coated with a mixture of materials, one of which is both acid insoluble and alkali insoluble and not otherwise degradable in the environments of both the stomach and intestine and the other of which is alkali soluble, but acid insoluble. A preferred acid insoluble and alkali insoluble material is a cellulose ether, most preferably, a lower alkyl cellulose ether, for example, ethyl cellulose. As the water soluble material, it is preferred to use a lower alkylene glycol, for example, propylene glycol. In preferred form, the alkali soluble, acid insoluble material is shellac.

Although good results can be achieved by the use of such sustained-released compositions, preparation thereof involves many steps, including the steps of coating the seed particles with the pharmaceutically-active compound. This step requires the use of an adhesive material and, depending on the particular way in which this step is carried out, it is either time-consuming or involves the use of special equipment.

In the case of drug molecules which are ionic in character, an alternative way of supporting the pharmaceutically-active material in the sustained release preparations is to affix it to particles of an ion exchange resin. Such preparations also require coatings.

An early patent relating to the preparation of ion exchange resin-drug particles to provide a sustained-release pharmaceutical is U.S. Pat. No. 2,990,332. However, the particles disclosed in this patent are uncoated, with there being only a short delay before the drug is released from the ion exchange resin into the gastrointestinal tract. In addition, the use of only cationic drugs is reported, whereas many pharmaceuticals comprise an anion as the active ion thereof, for example, theophyllinate which is the pharmaceutically-active anion of theophylline.

With respect to ion exchange resin-drug particles, the need for an effective coating is underscored by the fact that many pharmaceutically active ions, including anions, are relatively large in size and have a relatively small net charge, which may also be delocalized. Accordingly, the binding of the drug to sites on the ion exchange resin are relatively weak. Furthermore, gastric juice contains a relatively large concentration of chloride ions which are capable of rapidly displacing the bound ionic drug and binding tightly to the sites of the ion exchange resin. Thus, coatings which act as barriers to the ionic therapeutic are important to the clinical success of the product when controlled release over many hours in the intestine is desired.

U.S. Pat. No. 4,221,778 discloses the use of a fluidized coating technique in the coating of ion exchange resin-drug particles. Although the technique described in this patent is stated to be applicable to both anionic and cationic drugs, in fact only cationic drugs are provided as working examples.

The development of effective sustained release anionic drug-ion exchange resin pharmaceutical preparations has been hindered by several factors.

First, it has been difficult to develop anion exchange resins with a large enough number of anion exchange sites per resin bead to provide therapeutically useful dosing of weakly binding anions.

Second, the structure of anion exchange resin particles is typically reinforced by crosslinking. Resin particles swell during the hydration and rehydration steps necessary for their storage, coating and use as pharmaceutical preparations. Unchecked, swelling readily causes fracture of resin particles, and even if coated, substantial drug leakage would occur. Internal crosslinking of a resin polymer (such as divinylbenzene crosslinking of a styrene polymer) strengthens the resin structure but substantially reduces access of large anionic drugs to many of the resin exchange sites. Drug loading is thus seriously impaired. This phenomenon was recognized in U.S. Pat. No. 3,499,960 but not overcome.

Third, with many kinds of anion exchange resins the access by anionic drugs to exchange sites is further inhibited by secondary crosslinking. In the case of anion-exchange resins formed from quaternary ammonium cation substituted aromatic polymers, the reaction which places substituted ammonium onto the aromatic rings causes crosslinking between adjacent aromatic rings independent of any intended divinyl benzene crosslinking. Thus access by anionic drugs to exchange sites is further restricted.

The degree of crosslinking intended in the design of a resin is thus a compromise between maximum drug loading and maintaining the structural integrity of the resin particles. This, combined with the complication presented by secondary crosslinking, underscores the need to prevent those anions which are successfully bound from being prematurely discharged.

Fourth, and irrespective of the resin type selected, anionic drug-ion exchange resin complexes tend to have a very short shelf life due to dissociation rates considerably in excess of that seen in comparable cationic drug systems. Not surprisingly, disclosures for ionic drug-ion exchange resin systems have presented only examples for cationic therapeutics. See, for example, U.S. Pat. Nos. 3,143,465 and 3,594,470, and Borodkin, S., et al., *Journal of Pharmaceutical Sciences*, 60 (10), 1523-1527, (1971).

The present invention relates to improved anionic drug-ion exchange resin systems which can be used effectively to deliver anionic drugs in sustained release preparations.

SUMMARY OF THE INVENTION

In accordance with the present invention, there is provided in a method in which an ionizable pharmaceutical material having a pharmaceutically-active anionic group is bonded to an anion exchange resin having cationic groups bonded to displacable anions by bringing said material and said resin into contact with each other under conditions such that the pharmaceutically-active anionic group of said material is bonded to the cationic group of said resin and replaces the anions thereof, the improvement comprising effecting said contact in an environment which is substantially free of carbon dioxide and/or bicarbonate ion. A composition prepared by the method of this invention is also included within the scope of this invention.

It is believed that the invention will be practiced widely in the preparation of sustained-release pharmaceutical compositions which comprise theophylline. In such case, the theophyllinate ion (a negatively charged ion) is contacted with an anion exchange resin that includes cationic groups (positively charged ions such as, for example, quatenary ammonium) to which the theophyllinate ions bind. The contact is effected in an environment (both in the atmosphere and in solution) from which substantially all of bicarbonate/carbon dioxide has been removed and which is maintained substantially free of such materials.

An important advantage of the present invention is that it provides means for loading an anion exchange resin with greater amounts of pharmaceutical than is otherwise achieved. The following is believed to constitute an explanation of why the practice of the present invention results in the take-up by the ion exchange resin of relatively high amounts of pharmaceutical. In conventional use, a solution of the pharmaceutical contains bicarbonate ion that is derived from atmospheric $CO_2$ which comes into contact with the solution. It is believed that the bicarbonate ion competes with the pharmaceutical anion for resin binding sites, that is, the bicarbonate ion is preferably bound to the cationic groups of the resin relative to the pharmaceutical anion. The preferential effect is believed to be particularly severe with large anions that have a small net and/or delocalized charge, such as theophyllinate, which bind relatively weakly to the ion exchange sites. Thus, the bicarbonate ion is believed to interfere with the preparation of an efficacious drug-resin composition. The shelf life of such a composition is also seriously impaired unless care is taken to exclude carbon dioxide from contact with the product.

Accordingly, other aspects of this invention constitute:

(A) a pharmacologically active composition comprising an anion exchange resin having a predetermined binding capacity and a cationic group to which a pharmaceutically active anion is chemically bound and wherein at least about 40% of the binding capacity of the resin comprises said pharmaceutically active anion, such as, for example, theophyllinate; and (B) the provision of a method for retarding dissociation of a pharmaceutically active anion, (for example, theophyllinate) from an anionic resin exchange site comprising maintaining a composition comprising a pharmaceutically active anion chemically bound to a cationic group of an anion exchange resin in an environment which is substantially free of bicarbonate ion and/or carbon dioxide and a stable composition which is the result of practicing such method, that is, a composition in which the pharmaceutically active anions are maintained substantially localized at the exchange sites of the resin.

For those applications in which it is desired that the composition have sustained-release properties, ion exchange-loaded particles should be coated with an enteric coating. Accordingly, another aspect of the present invention comprises the provision of an enteric-coated, anionic drug-ion exchange resin pharmaceutical composition which exhibits sustained-release properties.

DETAILED DESCRIPTION OF THE INVENTION

Figure 1:
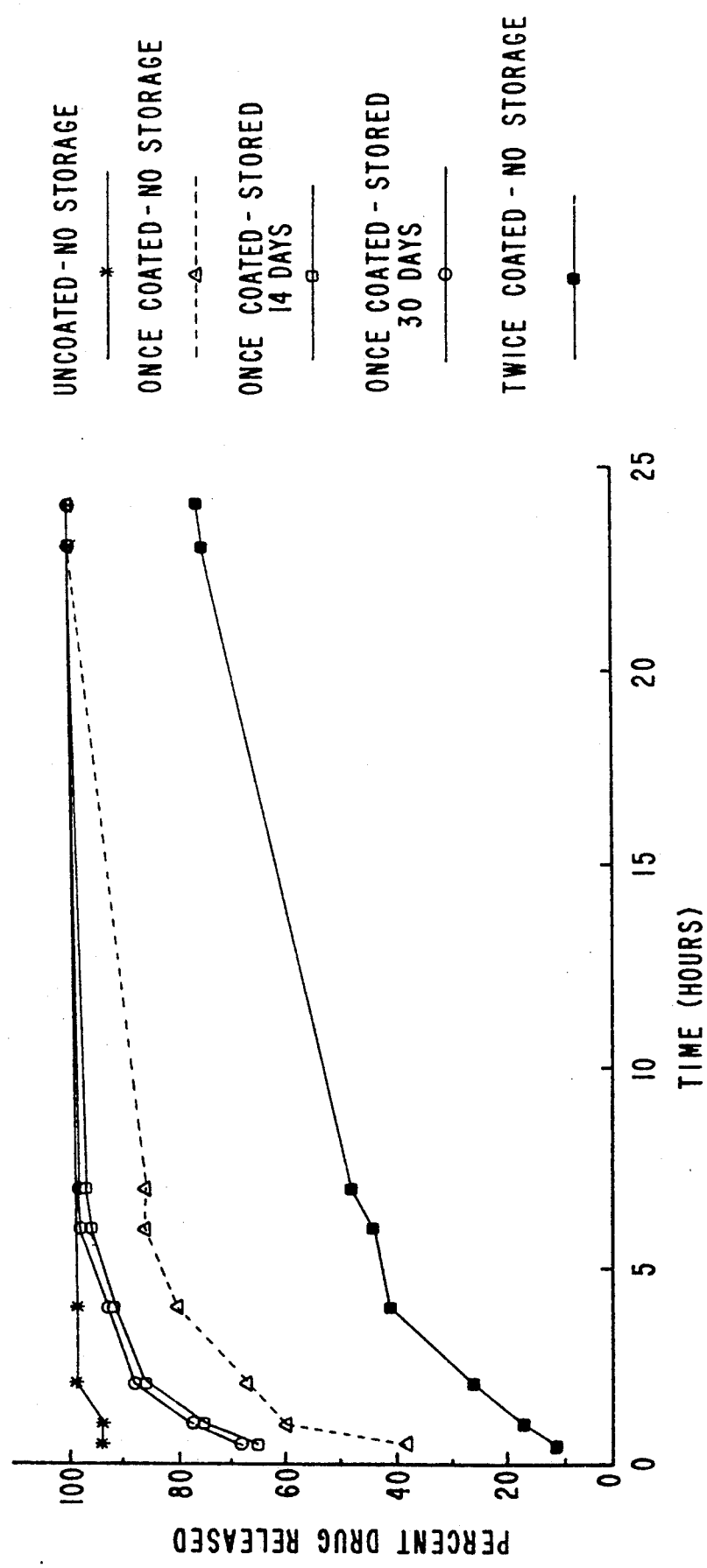
FIG. 1 is a graphical representation of the performance of compositions within the scope of the present invention and of a comparative composition.

Unless otherwise stated, the following terms have the meanings set forth below.

"Theophylline" means theophylline and derivatives thereof which are useful bronchodilators for the relief of asthma and which are useful in other therapeutic applications, including, for example, guaithylline (3,7-dihydro-1,3-dimethyl-1H-purine-2,6-dione), guaithylline compounded with 3-(2-methoxy phenoxy)-1,2-propanediol, theophylline diethanolamine, theophylline ethanolamine, and calcium theophyllinate compounded with calcium salicylate.

"Theophyllinate" means the anionic form of theophylline.

"Enteric coating" means a coating or combination of coatings which permit a therapeutic preparation to pass through the stomach substantially without being released into the stomach fluids and which permit the therapeutic preparation to be released into the intestines.

The essential elements and conditions used in the practice of this invention are an ionizable pharmaceutical material having a pharmaceutically-active anionic group, for example, theophylline and theophillinate respectively, and an anionic exchange resin having cationic groups bonded to displaceable anions, and an environment for contact of said pharmaceutical material and said resin which is substantially free of carbon dioxide and/or bicarbonate ion.

With respect to the pharmaceutical material, this invention may be practiced with any pharmaceutical which is soluble and which exits in ionic form in a semipolar or polar solvent, most typically water.

The present invention is particularly applicable to relatively bulky organic anionic pharmaceuticals with a relatively small net charge, especially if said charge is delocalized. Such substances typically do not gain access to a large number of the ion exchange resin's sterically inaccessible exchange sites and bind only weakly to the remaining accessible sites. Representative examples include theophyllinates, salicylates, and ibuprofen. It is also desirable to prevent dissociation of such molecules from the exchange sites of the resin.

Anion exchange resins for use in the practice of the present invention are typically made from monomer units which are joined to form a polymer backbone. The resins include a plurality of functional groups, that is, a cationic group bonded to a displaceable anion. The cationic groups, that is, positively-charged functional groups, are attached to the monomeric units of the polymer backbone at regular intervals and/or in specified amounts. In the presence of water, such as, for example, an aqueous solution of theophylline, the functional groups of the resin ionize, with the cationic groups attached to the polymer constituting the binding or exchange sites at which the anionic drug molecules are bonded chemically. Examples of such functional groups are primary, secondary and tertiary amines.

The individual polymer chains of the ion exchange resin are typically crosslinked with other similar polymer chains leading to a gel-like, insoluble, bead-formed composition which represents the typical anion exchange resin particle.

Crosslinking, however, has the effect of impeding access by anions to the ionic binding sites located within the resin structure. Accordingly, the effective capacity of resins to bind large anions, such as, for example, theophyllinate, is typically much reduced compared with the binding of small inorganic anions such as, for example, chloride.

Anion exchange resins composed of aromatic monomers may exhibit further reduced binding capacity for relatively large anions because of undesired secondary crosslinking which stems from side reactions which take place during the reaction by which functional groups such as ammonium or quatenary ammonium exchange groups are attached to the polymer backbone.

Anion exchange resins, including species of non-toxic resins, are available in a wide variety of bead sizes and exchange capacities. It is expected that a considerable variety of anion exchange resins representing a broad spectrum of ion binding capacities, bead or particle sizes, and degrees of crosslinking will be useful in the practice of this invention, and will show useful and significant improvements in binding of anionic pharmaceuticals when binding is effected in the absence of carbon dioxide and/or bicarbonate.

In the practice of the present invention, it is preferred to use anion exchange resin gel type beads which include about 1 to about 15% of crosslinking. Such beads are commercially available. It should be understood that resins with greater degrees of crosslinking can be used in the practice of this invention, particularly in applications involving pharmaceuticals having relatively small anionic groups.

For use in pharmaceutical applications, the anion exchange resin must be devoid of toxicological effects. Non-toxic ion exchange resins for use in the practice of the present invention are available commercially.

Examples of suitable anion exchange resins are those made from polymers assembled from monomeric units of styrene, divinylbenzene, acrylic acid and acrylamide, methacrylic acid and methacrylamide, and condensation products of aliphatic polyamines with formaldehyde or with alkyl dihalides. All of the above monomeric units are additionally substituted prior to or after polymerization to confer particular ion exchange capabilities or to otherwise modify the properties of the resin.

Resins with a broad range of binding capacities can be used in the practice of the present invention. It is preferred that the resin have a binding capacity of at least about 25%, more preferably about 50% or higher. Binding capacity is measured for each species of interest according to the amount of said species removed from a suitably concentrated solution.

The size of resin particles useful in the practice of the invention can vary over a broad range, for example, about 10 $\mu$m to 2000 $\mu$m in diameter. Particles of commercially available gel-type, bead-formed resins are normally in the range of about 75 to about 1000 μm in diameter.

Examples of commercially available gel-type anion exchange resins useful in the practice of this invention include: products IRA 400, IRA 402, IRA 401s, and IRP 276 (divinylbenzene crosslinked styrene polymers with 8, 6, 4 and 2 percent crosslinking respectively) of Rohm and Haas Company, Philadelphia, Pa.; products DOW XYS 40013-00, DOWEX 1×4, DOW XF43311-01 (also styrene polymers with 8, 4 and 2 percent crosslinking respectively) of Dow Chemical Company, Midland, Mich.; and product IRA 458 (a 4 percent divinylbenzene crosslinked methacrylate) of Rohm and Haas Company.

Improved theophyllinate binding and resin-drug complex stability can be demonstrated for all of the above resins. Test work has shown that products IRA 400 and DOW XYS 40013-00 exhibit particularly good stability against premature drug loss caused by inadvertent particle rupture and that products IRP 276 and DOW XF 43311-01 have particularly high binding capacity.

As mentioned above, the conditions under which the pharmaceutical material and anion exchange resin are contacted involve an environment which is substantially free of carbon dioxide and/or bicarbonate ion. For explanatory purposes, it is noted that carbon dioxide is present in the atmosphere at a mole fraction of about 0.02%. When atmospheric carbon dioxide comes into contact with an aqueous composition, it is dissolved therein and then chemically combines with water to form carbonic acid, $H_2CO_3$. Some of the carbonic acid will dissociate to form negatively charged bicarbonate ion, $HCO_3$. Formation of bicarbonate from carbonic acid is favored under alkaline conditions and is prevented under highly acidic conditions. In connection with the principles underlying the application of the present invention, it is believed that the bicarbonate ion which is derived from atmospheric carbon dioxide competes effectively with anionic pharmaceuticals, such as theophyllinate, for binding sites on anion exchange resins.

In accordance with the present invention, any suitable manipulative steps and types of apparatus can be used to minimize the effects of bicarbonate/$CO_2$ on the binding of the pharmaceutical material to the anionic exchange resin. There follows a description of guidelines and preferred steps for use in the practice of the present invention.

Gel-type anion exchange resin beads, which are preferably used in the practice of this invention, are typically obtained in dehydrated form. It is preferred that the particular steps and manipulations selected to initially hydrate the resin beads also be designed to exclude or minimize contamination of the beads by carbon dioxide and bicarbonate. If this is not done, their presence may to some extent (dependent on the relative binding affinities of the pharmaceutical material and bicarbonate) interfere with later maximal loading of the beads. In preferred form, the dehydrated beads are suspended in an excess of degassed, deionized water with mixing which is accomplished in a $CO_2$-free atmosphere such as, for example, under nitrogen gas. Deionized water may be degassed by placing it in a flask with gentle stirring under a partial vacuum of about 100 mm Hg for one-half hour or by boiling and cooling, with cooling accomplished under a nitrogen atmosphere.

Commercially prepared bead-formed anion exchange resin particles should also be hydrated with reference to the manufacturer's instructions so as not to mechanically damage the particles by shearing or excessively vigorous stirring. In the practice of this invention, it will be generally satisfactory to slowly hydrate the resin particles in a sample of deionized, degassed water maintained at room temperature with gentle stirring for 24 hours or less.

The hydrated resin beads may then be collected by generally accepted methods such as, for example, by low speed centrifugation, again with reference to any specific recommendations of the manufacturer.

The hydrated resin beads are then placed into an excess volume of degassed, deionized aqueous solution of the pharmaceutical material.

The unequilibrated mixture of resin beads and aqueous solution of pharmaceutical material is preferably allowed to undergo ion exchange in an environment which is substantially free of carbon dioxide. For example, this can be effected in a centrifuge tube, having an airtight cap, with any gas under the cap being of a kind which is carbon dioxide-free, such as nitrogen gas. The mixture is then gently rotated, again with reference to any restrictions suggested by the resin manufacturer, for a period of time sufficient to accomplish ion exchange. Exemplary of conditions which have been used effectively include a time of reaction of about 24 hours in a centrifuge tube utilizing gentle rotation of about 20 rpm.

The loading of the pharmaceutical can be monitored by removing small samples of the supernatant solution, with care taken to assure that the resin particles have settled, and measuring the decrease in absorbance of the solution at a suitable wavelength.

After ion exchange is complete, the resin particles loaded with the pharmaceutical can be collected in any suitable way. This can be done, for example, by low speed centrifugation. The drug-loaded particles can be resuspended in an excess volume of degassed, deionized water to remove unbound pharmaceutical and those anions displaced from the anion exchange resin. The particles may then be recollected, for example, by low speed centrifugation.

The drug-loaded particles are then dried, for example, by placing them in an oven under a nitrogen atmosphere at about 60° C. for a period of about 24 hours or to a moisture level of about 5 to 10%.

Pending furthering processing steps, the drug loaded particles should be maintained under conditions which prevent or inhibit dissociation of the anionic drug molecules from the exchange sites of the resin particles. Such conditions include maintaining the drug-loaded particles in an environment which precludes contamination by carbon dioxide and/or bicarbonate ion. This enables the particles to be stored for long periods, for example, a year or more, while the efficacy of the drug-loaded particles is maintained. For this purpose, the dry drug-loaded particles can be stored in a sealed container which prevents their being contacted by water vapor and/or carbon dioxide.

For the purpose of preparing a sustained-release pharmaceutical composition from the drug-loaded particles, they should be coated with a material which prevents or deters release and absorption of the pharmaceutically-active anion from the exchange sites of the resin until the particles reach the intestines. Accordingly, they can be coated with a suitable enteric coating.

It is noted that the fluids of the digestive tract contain a considerable number of species of anions, including anions which have high affinities for ion exchange resins and which are thus capable of displacing prematurely the pharmaceutically-active anion affixed to the resin particles. For example, the stomach fluids contain such an anion in the form of about 0.1M of chloride ion. In order to confer sustained-release properties on drug-loaded particles, such as, for example, theophyllinate-loaded resin particles, it is necessary to apply to the particles a coating which permits the particles to pass through the stomach without release of the theophyllinate into the stomach fluids. If this is not done, the theophyllinate ions would be rapidly discharged into the stomach fluids and the blood stream with attendant adverse side effects of the type mentioned hereinabove being encountered.

Any suitable enteric coating can be applied to the drug-loaded particles, including enteric coatings of the type that permit ions such as chloride (for example, from gastric juice) to diffuse into the coated resin particles where they displace the negatively-charged drug from a resin binding site, but in a manner such that the drug leaves the coated particle at a rate so slow that sustained release is achieved in the small intestine of the patient.

The following publications disclose examples of types of enteric coatings that can be used in the practice of the present invention or that can be adapted for use in the practice of the present invention. U.S. Pat. No. 3,109,775 discloses the coating of sustained-release particles with a cellulose ester mixture, cellulose acetate-phthalate, which is a material unaffected by acidic stomach fluids, but which dissolves slowly in mildly alkaline intestinal fluids. U.S. Pat. No. 4,663,150 discloses coating materials made from water soluble polymers, water insoluble polymers, and mixtures thereof, including materials such as hydroxypropyl methyl cellulose, copolymers of acrylic and methyacrylic acid esters, polyvinylpyrrolidone, ethyl cellulose, shellac and lacquers. PCT application bearing Publication No. WO 87/06098 discloses a coating derived from an ethanol based solution of a cellulose ether and propylene glycol which is dried to create a water permeable membrane.

A preferred method of coating anion exchange resin particles which have been previously loaded according to this invention is the procedure described in U.S. Pat. No. 4,221,778. According to the '778 patent, the theophyllinateanion exchange resin complexed particles are coated with a highly hydrophilic substance, such as poly(ethylene glycol), prior to applying an enteric coating. The poly(ethylene glycol) is presumed to maintain the resin particles in a partially hydrated state thereby preventing fracture of the loaded particles which tends to be caused by hydration changes normally associated with the preparation or use of the particles. The fracture-resistant particles are then coated with ethyl cellulose using vegetable oil to plasticize the coating.

If the coated particles are to be stored before use, it is preferred that they be placed in a container from which moisture is excluded.

For use in pharmaceutical applications, it is preferred that the coated particles be suspended in a solution of degassed, deionized water and packaged in an airtight container such as, for example, a toothpaste-type tube. Such coated particles may be further compounded with excipients such as, for example, flavorings, colorings, sweeteners, gum thickeners, or preservatives of the type available in the art and which are of nonionic character. The compounded suspension of coated particles may thus take the form of a liquid suspension, a gel, or a paste. An advantage of the present invention is that, in such form, the particles can be dispensed in a variable dose from a container such as, for example, a toothpaste-type tube. By way of background, it is noted that sustained release "anion" pharmaceuticals of the prior art are typically available in capsule form. This limits available doses to specified amounts and multiples thereof. For many therapeutics such as theophyllinate, it is clinically desirable to carefully optimize the dose to each individual patient, especially in the case of children. The present invention provides physicians with a sustained release product which also allows for variable dosing. Still another advantage of the present invention is that the liquid suspension, gel, or paste form is much easier to swallow (especially for children and older persons) than capsules.

EXAMPLES

The following examples are illustrative of the preparation of sustained release anionic drug formulations of the present invention.

EXAMPLE 1

This example illustrates the preparation of a sustained release pharmaceutical composition comprising theophyllinate bound to an anion exchange resin.

A gel-type quaternary amino substituted styrene polymer containing 8% of divinylbenzene crosslinking formed into approximately spherical beads having a diameter of about 50 to about 100 microns was utilized as the anion exchange resin (IRA 400 from Rohm and Haas Company, Philadelphia, Pa.). The resin was allowed to swell by placing about 100 grams of dried particles in about 1000 ml degassed, deionized water which was then placed in a 2000 ml flask. The deionized water was degassed by subjecting it to a vacuum equivalent to about 100 mm Hg with gentle stirring. The flask was then made airtight and the remaining airspace was filled with a carbon dioxide-free atmosphere of nitrogen gas. The sample was gently stirred at about 20 rpm for about 24 hours at room temperature.

The hydrated resin is then filtered and placed in 2000 ml container containing about 1000 ml of deionized water (degassed as above) and about 100 grams of theophylline, the source of which was aminophylline. The sample is sealed under an airtight cap as above and then rotated at about 20 rpm for 24 hours at room temperature. Drug loading is confirmed by measured the loss of free theophyllinate from solution by measurement of the UV absorbance at 280 mm.

The loaded particles are collected by filtration and washed free of exchange salts with about 1 liter of $CO_2$-free, bicarbonate-free deionized water and then dried at 60° C. until a moisture level of about 5 to 10% is achieved.

Calculations show that the amount of theophyllinate affixed to the resin beads comprises about 40–50 wt. % of the drug-resin complex.

The dried drug resin complex particles (about 100 to 200 g) are then mixed into a $CO_2$-free sample of deionized degassed water containing 10% of a high molecular weight hydrophilic glycol polymer (with a mean molecular weight of about 3400 daltons) such as poly-(ethylene glycol) (3350 from Union Carbide Corporation, New York). The poly(ethylene glycol) solution is allowed to contact the particles for about 24 hours until the particles adsorb an amount of glycol equal to 20-25% of the dry weight of the untreated particles.

The poly(ethylene glycol)-impregnated fracture-resistant particles are then dried in an oven at 60° C. to a maximum moisture level of 5%, according to the procedure of "Weight Loss on Drying" using an O'-Haus Moisture Balance.

The particles are then placed in an air suspension coating apparatus (Wurster Dairy Equipment Co., Madison, Wis.).

The particles are finally coated with a mixture of ethyl cellulose/vegetable oil of proportions 2.5:1 (w/w) in a volatile solvent mixture of methylene chloride/acetone 10:1 (v/v) or water-free ethanol. The ethyl cellulose utilized is ethyl cellulose 50 cps, NF Grade, from Dow Chemical Company, Midland, Mich. The vegetable oil is a refined grade, Durkex 500 from Durkee Foods Division, SCM Corporation, Rockville Center, N.Y. The coating solution was sprayed at a rate of about 10 ml/min. Inlet temperature was about 150° F. and outlet temperature was about 100° F. The entire application time was about three hours.

The coated particles are then dried in the same air suspension coating apparatus to a maximum moisture level of 5%, according to the procedure of Weight Loss on Drying using an O'Haus Moisture Balance, and stored in a sealed container under a $CO_2$-free atmosphere.

This next example is illustrative of the effective sustained-release properties of coated particles prepared according to the practice of this invention.

EXAMPLE 2

IRA 400 resin particles containing theophyllinate and impregnated with polyethylene glycol 3350, as described in Example 1, were double coated with plasticized ethyl cellulose, resulting in a 13% w/w coat.

FIG. 1 demonstrates the substantially enhanced drug retention of the coated particles when resuspended in gastric fluid compared with the drug retention of uncoated or single coated preparations. The resultant performance is comparable with effective sustained release anionic drug composition not dependent on ion exchange resins, such as, for example, those described in aforementioned Publication No. WO 87/06098.

Although large anions may be displaced easily from the resin exchange sites within a coated resin particle by entering chloride ions, such as those present in gastric fluid, such anions move only slowly outwardly past the water permeable diffusion barrier of the coated particles. Thus actual displacement of theophyllinate from the coated particles is much retarded, and sustained release properties are conferred.

The desorption profile of an anionic drug can thus be lengthened or shortened (see FIG. 1) by changing the thickness or number of the coating layers. The same effective result can be achieved by dispensing a clinical preparation which contains a mixture of particles with different coating thicknesses.

The next example is illustrative of the dramatic effect of carbon dioxide on complexes of theophyllinate and an anion exchange resin.

EXAMPLE 3

In this example, theophyllinate anions are loaded onto IRA 400 ion exchange resin particles according to the procedure of Example 1. The loaded particles are washed free of exchange salts, and then placed in deionized water. The particles are not coated with ethyl cellulose or treated with poly(ethylene glycol). In the absence of an available source of exchanging ions, dissociation of theophyllinate anions from the resin should be minimal.

Figure 2:
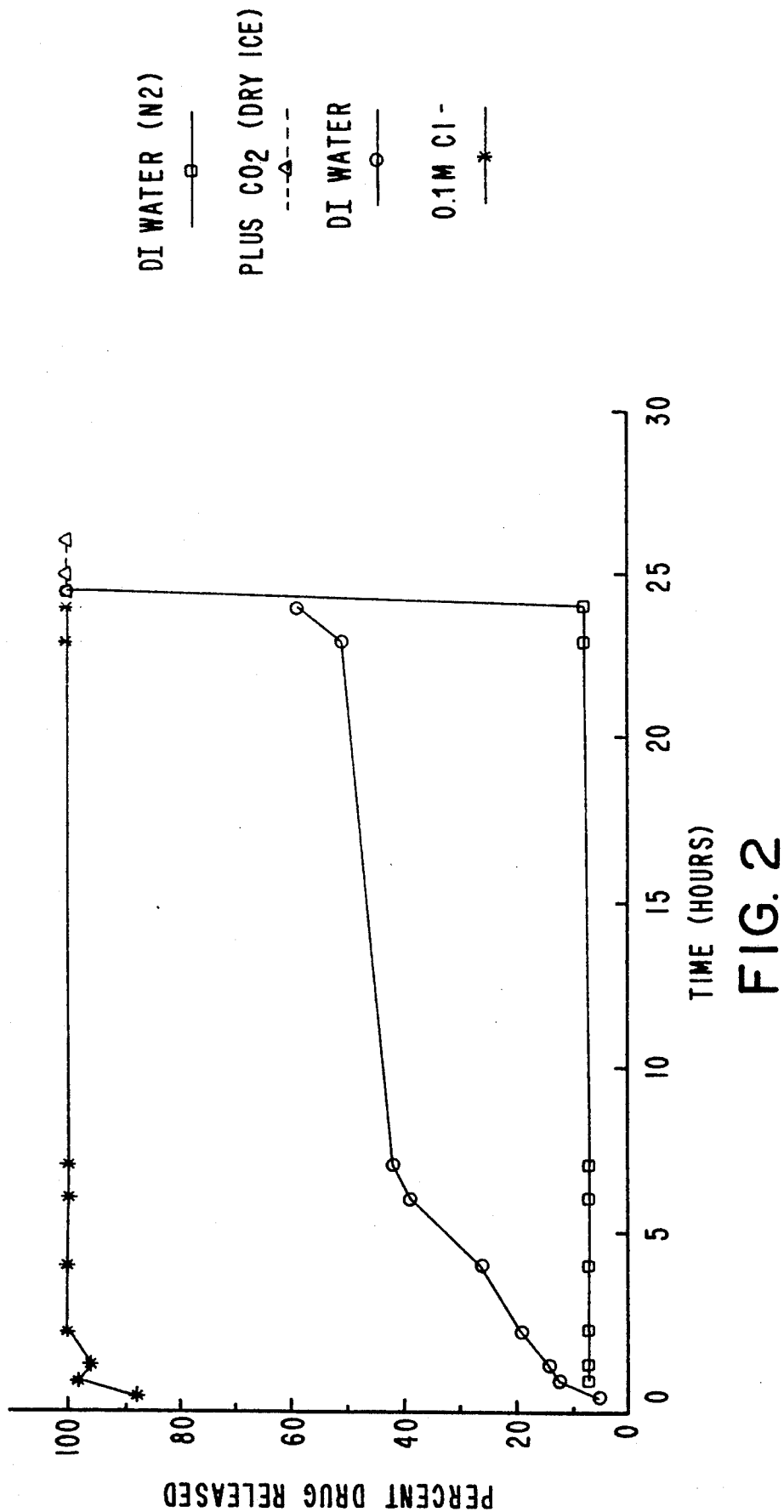
FIG. 2 is a graphical representation of the evaluation of compositions within the scope of the present invention under various conditions.

As is evident from the data reported in FIG. 2, when the loaded particles are placed in deionized water which is maintained under nitrogen gas, leakage of theophyllate is prevented. Consistent with the novel discovery of this invention, the addition of dry ice to loaded resin particles which have been stable for over 20 hours caused almost immediate release of the theophyllinate ions. This underscores the importance of this invention with respect to the production and storage of sustained release anionic drug preparations.

As is also evident from the data reported in FIG. 2, sufficient bicarbonate ion is generally present in deionized water to cause undesired displacement of bound theophyllinate. (Freshly distilled water left to equilibrate with the atmosphere soon acquires a pH of about 6.) This is also encountered by adding 0.1M $Cl^-$, which simulates the ion effects of gastric fluid.

Thus sustained release preparations of anionic drugs can be made effective by first loading the resin particles under conditions which exclude carbon dioxide and then providing such particles with a coating sufficient to retard diffusion of the drug molecules out of the particles when they encounter an environment (gastric juice) laden with competing anions.

What is claimed is:

1. In a method in which an ionizable pharmaceutical material having a pharmaceutically-active anionic group is bonded to particles of an anion exchange resin having cationic groups bonded to displacable anions by bringing a solution of said material and said particles of resin into contact with each other under conditions such that the pharmaceutically-active anionic group of said material is bonded in a predetermined amount to the cationic group of said resin and replaces the anion thereof, the improvement comprising effecting said contact in an environment which is substantially free of carbon dioxide and/or bicarbonate ion, to thereby increase the amount of said anionic group bonded to said particles relative to said predetermined amount, wherein said pharmaceutical material is theophylline and said anionic group is theophyllinate.

2. A method according to claim 1 wherein an aqueous solution of said pharmaceutical material substantially free of bicarbonate ion is contacted with said resin in the form of hydrated beads which are substantially free of bicarbonate ion.

3. A method according to claim 1 wherein said resin is crosslinked.

4. A method according to claim 1 wherein said resin is a gel-type quaternary amine derivative of a crosslinked styrene polymer.

5. A pharmacologically active composition comprising a plurality of particles of an anion exchange resin having cationic groups, wherein pharmaceutically active anions are chemically affixed to said cationic groups, wherein said composition is substantially free of bicarbonate, and wherein said pharmacologically active anions are theophyllinate.

6. A composition according to claim 5 wherein said composition is in the form of particles coated with an enteric coating.

7. A pharmacologically active composition comprising: (A) an anion exchange resin having a predetermined binding capacity and a cationic group; and (B) a pharmaceutically active anion which is chemically bound to said group, wherein at least about 40% of the binding capacity of the resin comprises said pharmaceutically active anion, wherein said pharmaceutically active anion is theophylliate.

8. A composition according to claim 7 wherein at least about 50 wt. % of the binding capacity of the resin comprises said pharmaceutically active anion.

9. A pharmaceutical composition comprising particles of the composition of claim 5 coated with an enteric coating.

10. A method for providing prolonged continuous release of a pharmaceutically active anion within the gastrointestinal tract of a patient comprising ingestion by the patient of a composition according to claim 9.

11. A method according to claim 1 wherein the solution of said material includes a semi-polar or polar solvent.

12. A method according to claim 11 wherein said solution is an aqueous solution.

13. In a composition comprising theophyllinate which is a pharmaceutically-active anionic group of theophylline which is an ionizable pharmaceutical material, said theophyllinate being bound to a cationic group of an anion exchange resin, said composition having a predetermined rate of dissociation, the improvement comprising the combination of said composition and an environment which is substantially free of carbon dioxide and/or bicarbonate ion, wherein the rate of dissociation of the composition of said combination is lower than said predetermined rate.

14. A composition according to claim 13 wherein said environment is an aqueous environment.

15. A composition according to claim 13 including an enteric coating.

* * * * *